United States Patent
Woodward et al.

(10) Patent No.: US 12,205,285 B2
(45) Date of Patent: Jan. 21, 2025

(54) LUNG ANALYSIS AND REPORTING SYSTEM

(71) Applicant: GYRUS ACMI, INC., Westborough, MA (US)

(72) Inventors: Cyndi Woodward, Framingham, MA (US); Greg Little, Sammamish, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 146 days.

(21) Appl. No.: 17/806,180

(22) Filed: Jun. 9, 2022

(65) Prior Publication Data

US 2022/0405925 A1 Dec. 22, 2022

Related U.S. Application Data

(60) Provisional application No. 63/259,906, filed on Jun. 16, 2021.

(51) Int. Cl.
*G06T 7/00* (2017.01)
*G06T 7/149* (2017.01)
(Continued)

(52) U.S. Cl.
CPC ............ *G06T 7/0012* (2013.01); *G06T 7/149* (2017.01); *G06T 19/00* (2013.01); *G06V 20/64* (2022.01);
(Continued)

(58) Field of Classification Search
CPC ....... G06T 7/0012; G06T 7/149; G06T 19/00; G06T 2207/30061; G06T 2210/41;
(Continued)

(56) References Cited

U.S. PATENT DOCUMENTS 11,090,121 B2 * 8/2021 Culala .................. G06T 19/003
2019/0325645 A1 10/2019 Guendel et al.
(Continued)

FOREIGN PATENT DOCUMENTS

| CN | 117813625 A | 4/2024 |
|---|---|---|
| DE | 112022003105 | 7/2024 |
| WO | 2022266587 | 12/2022 |

OTHER PUBLICATIONS

"International Application Serial No. PCT US2022 072855, International Search Report mailed Oct. 11, 2022", 5 pgs.
(Continued)

*Primary Examiner* — Antonio A Caschera
(74) *Attorney, Agent, or Firm* — Schwegman Lundberg & Woessner, P.A.

(57) ABSTRACT

Systems, methods, and executable programs for providing lung candidacy information to health care professionals. A method includes receiving three-dimensional image data categorized as lung lobe voxels, airway voxels, or lung fissure voxels. A fissure integrity score is generated for the lung fissure voxels. First perspective transparent views of the categorized lung lobe voxels, the categorized airway voxels, and the categorized lung fissure voxels are generated based on a first point of view. The first perspective view of the lung fissure voxels includes a visual representation of fissure integrity based on the generated fissure integrity scores for the corresponding voxels. A report is generated that includes the generated views. The report is outputted.

19 Claims, 6 Drawing Sheets

(51) Int. Cl.
  *G06T 19/00* (2011.01)
  *G06V 20/64* (2022.01)
  *G16H 15/00* (2018.01)
  *G16H 30/40* (2018.01)

(52) U.S. Cl.
  CPC .............. *G16H 15/00* (2018.01); *G16H 30/40* (2018.01); *G06T 2207/30061* (2013.01); *G06T 2210/41* (2013.01); *G06T 2219/004* (2013.01); *G06V 2201/031* (2022.01)

(58) Field of Classification Search
  CPC ... G06T 2219/004; G06T 15/08; G16H 15/00; G16H 30/40; G06V 20/64; G06V 2201/031
  See application file for complete search history.

(56) References Cited

U.S. PATENT DOCUMENTS

| | | | |
|---|---|---|---|
| 2019/0350659 A1* | 11/2019 | Wang | A61B 8/0841 |
| 2020/0222120 A1 | 7/2020 | Culala | |
| 2022/0036985 A1* | 2/2022 | Culala | G16H 20/40 |

OTHER PUBLICATIONS

"International Application Serial No. PCT US2022 072855, Written Opinion mailed Oct. 11, 2022", 8 pgs.

Althof, Zachary W, "Automatic Quantification of Pulmonary Fissure Integrity: a Repeatability Analysis", 2020 IEEE 17th International Symposium on Biomedical Imaging (ISBI), IEEE, (Apr. 3, 2020), 581-585.

"International Application Serial No. PCT US2022 072855, International Preliminary Report on Patentability mailed Dec. 28, 2023", 10 pgs.

"German Application Serial No. 11 2022 003 105.0, Office Action mailed Mar. 13, 2014", w/o English translation, 3 pgs.

"German Application Serial No. 11 2022 003 105.0, Response filed Jun. 6, 2024 to Office Action mailed Mar. 13, 2014", W/English Claims, 35 pgs.

* cited by examiner

LUNG ANALYSIS AND REPORTING SYSTEM

CROSS-REFERENCE TO RELATED APPLICATION

This application claims the benefit of priority to U.S. Provisional Patent Application Ser. No. 63/259,906 filed Jun. 16, 2021, the contents of which are incorporated herein by reference in their entirety.

BACKGROUND

Analysis of the patient's high-resolution computed tomography (HRCT) information and quantitative computed tomography (QCT) results are critical to successful patient outcomes. Reliable key measures of emphysema severity, fissure integrity, and heterogeneity are needed to allow physicians to quickly and confidently identify a target lobe and potential candidates for treatment in order to ensure a successful bronchoscopy guided lung volume reduction (BLVR) procedure.

SUMMARY

The present disclosure provides systems, methods, and executable programs for providing lung candidacy information to health care professionals.

In an illustrative embodiment, a method includes receiving three-dimensional image data of at least a portion of a lung having lung fissures, the three-dimensional image data comprises voxels, categorizing the voxels as at least one of lung lobe voxels, airway voxels, or lung fissure voxels, generating a fissure integrity score for each of the lung fissure voxels based on at least one of a predefined radio density value threshold or a radio density value threshold range, generating a first perspective transparent view of the categorized lung lobe voxels based on a first point of view, generating a first perspective view of the categorized airway voxels based on the first point of view, generating a first fissure perspective view of the categorized lung fissure voxels associated with a first one of the lung fissures based on the first point of view, wherein the first perspective view of the lung fissure voxels includes a visual representation of fissure integrity based on the generated fissure integrity scores for the corresponding voxels; and generating a report comprising the generated views, and outputting the report.

In another illustrative embodiment, a system includes a processing device, a memory, and an output device. The memory is configured to store computer-readable instructions configured to cause the processing device to receive three-dimensional image data of at least a portion of a lung having lung fissures, categorize the voxels as at least one of lung lobe voxels, airway voxels, or lung fissure voxels, generate a fissure integrity score for each of the lung fissure voxels based on at least one of a predefined radio density value threshold or a radio density value threshold range, generate a first perspective transparent view of the categorized lung lobe voxels based on a first point of view, generate a first perspective view of the categorized airway voxels based on the first point of view, and generate a first perspective view of the categorized lung fissure voxels associated with a first one of the lung fissures based on the first point of view, wherein the first perspective view of the lung fissure voxels includes a visual representation of fissure integrity based on the generated fissure integrity scores for the corresponding voxels; and generate a report comprising the generated views. The output device in signal communication with the processing device. The output device is configured to output the report.

In another illustrative embodiment, a non-transitory computer-readable recording medium with an executable program stored thereon. The program is configured to cause a processor to receive three-dimensional image data of at least a portion of a lung having lung fissures, the three-dimensional image data comprises voxels, categorize the voxels as at least one of lung lobe voxels, airway voxels, or lung fissure voxels, generate a fissure integrity score for each of the lung fissure voxels based on at least one of a predefined radio density value threshold or a radio density value threshold range, generate a first perspective transparent view of the categorized lung lobe voxels based on a first point of view, generate a first perspective view of the categorized airway voxels based on the first point of view, generate a first perspective view of the categorized lung fissure voxels associated with a first one of the lung fissures based on the first point of view, wherein the first perspective view of the lung fissure voxels includes a visual representation of fissure integrity based on the generated fissure integrity scores for the corresponding voxels, generate a second perspective transparent view of the categorized lung lobe voxels based on a second point of view, generate a second perspective view of the categorized airway voxels based on the second point of view, generate a second perspective view of the categorized lung fissure voxels associated with a second one of the lung fissures based on the second point of view, wherein the second perspective view of the lung fissure voxels includes a visual representation of fissure integrity based on the generated fissure integrity scores for the corresponding voxels, generate a third perspective transparent view of the categorized lung lobe voxels based on a third point of view, generate a third perspective view of the categorized airway voxels based on the third point of view, generate a third perspective view of the categorized lung fissure voxels associated with a third one of the lung fissures based on the third point of view, wherein the third perspective view of the lung fissure voxels includes a visual representation of fissure integrity based on the generated fissure integrity scores for the corresponding voxels, generate a report comprising the generated views, and output the report.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely illustrative in nature and is not intended to limit the present disclosure, application, or uses. The following description explains, by way of illustration only and not of limitation, various embodiments of devices and methods for analyzing and providing a comprehensive report for use in determining candidacy of lung lobes for a pending bronchoscopy guided lung volume reduction (BLVR) procedure.

An embodiment describes a process to automate, display, interact with and characterize aspects of the lung. When the human lung is imaged in vivo with an imaging acquisition device, that image can be reconstructed and evaluated to depict normal and diseased states. Because of the various subclasses of disease and the various depictions (phenotypes) of a disease entity, evaluation of lobular regions of the lung and the fissures separating them are important to accurately characterize disease and predict response to BLVR therapy.

This disclosure includes systems and methods to provide visualization of lung lobes, completeness of fissures and values related to the extent of emphysema in an automated way to enable clinical decision making.

The left and right lungs are each divided into a plurality of lobes by deep clefts, which are the interlobar fissures, referred to herein simply as fissures. The outer surface of the lungs is lined by pleura, including an inner layer which is the visceral pleura which dips into the fissures to surround the lobes. The fissures therefore are the joints between the lobes of the lung and are defined by the outermost surface of the lobes and the visceral pleura at the locations where the lobes abut each other. Therefore, although the fissure itself is actually an interface between abutting lobes, it is the very thin layer of the lobar interfaces that can be detected on a volumetric image and is interpreted as being the fissure. The right lung includes three lobes (the upper, middle, and lower lobes) which are divided by two fissures, known as the oblique and the horizontal fissures. The left lung includes two lobes (the upper and lower lobes) with one fissure, the oblique fissure, between them.

The edges of the lobes and the pleura that lines the lobes define the fissures and separate the lobes such that the ventilation of each lobe separates from that of adjacent abutting lobes. In addition, the pleura normally form a smooth surface, allowing abutting lobes to slide relative to each other during inhalation and exhalation. However, in certain disease conditions, the pleura may become thickened or adherent. In addition, abutting lobes may adhere to each other and the pleura and lung margins that normally define the fissure may be lost. The fissure is described by a level of completeness and below a certain level air can flow between the lobes. Various embodiments described herein identify the fissure completeness using volumetric radiological images and present them visually in a 2D image.

Figure 1:
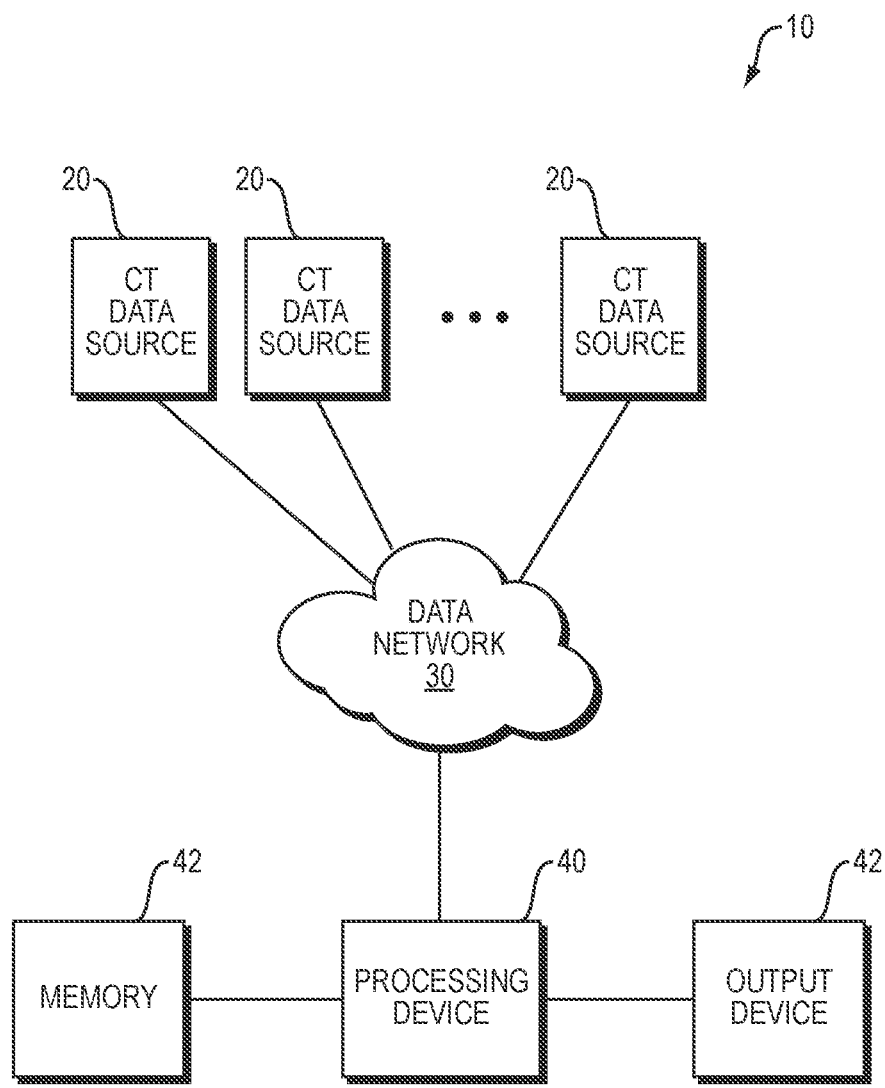
FIG. 1 is a block diagram of an exemplary system formed in accordance with an embodiment of the present invention.

FIG. 1 shows an exemplary lung visualization system 10, which may include a processing device 40, such as a processor in a computer, and an output device 42, such as a visual display (monitor or screen) or a printing device. The system 10 may also include instructions included in software (computer readable media), stored in a memory 44 of the system 10, and operable on/by the processing device 40. The software may include instructions for the processing device 40 to perform the various steps and methods described herein, including instructions to receive patient data including volumetric imaging data from data sources 20 possibly connected to the processing device 40 via a public and/or private data network 30, analyze the data to characterize the lung, and generate images resulting from the analysis of the imaging data. The generated images may be transmitted to a customer computing device via the data network 30 or may be outputted in a physical form and delivered to the customer.

Examples of the embodiments may be implemented using a combination of hardware, firmware, and/or software. For example, in many cases some or all of the functionality provided by examples may be implemented in executable software instructions capable of being carried on a programmable computer processor. Likewise, some examples of the invention include a computer-readable storage device on which such executable software instructions are stored. In certain examples, the system processor itself may contain instructions to perform one or more tasks. System processing capabilities are not limited to any specific configuration and those skilled in the art will appreciate that the teachings provided herein may be implemented in a number of different manners.

Figure 2:
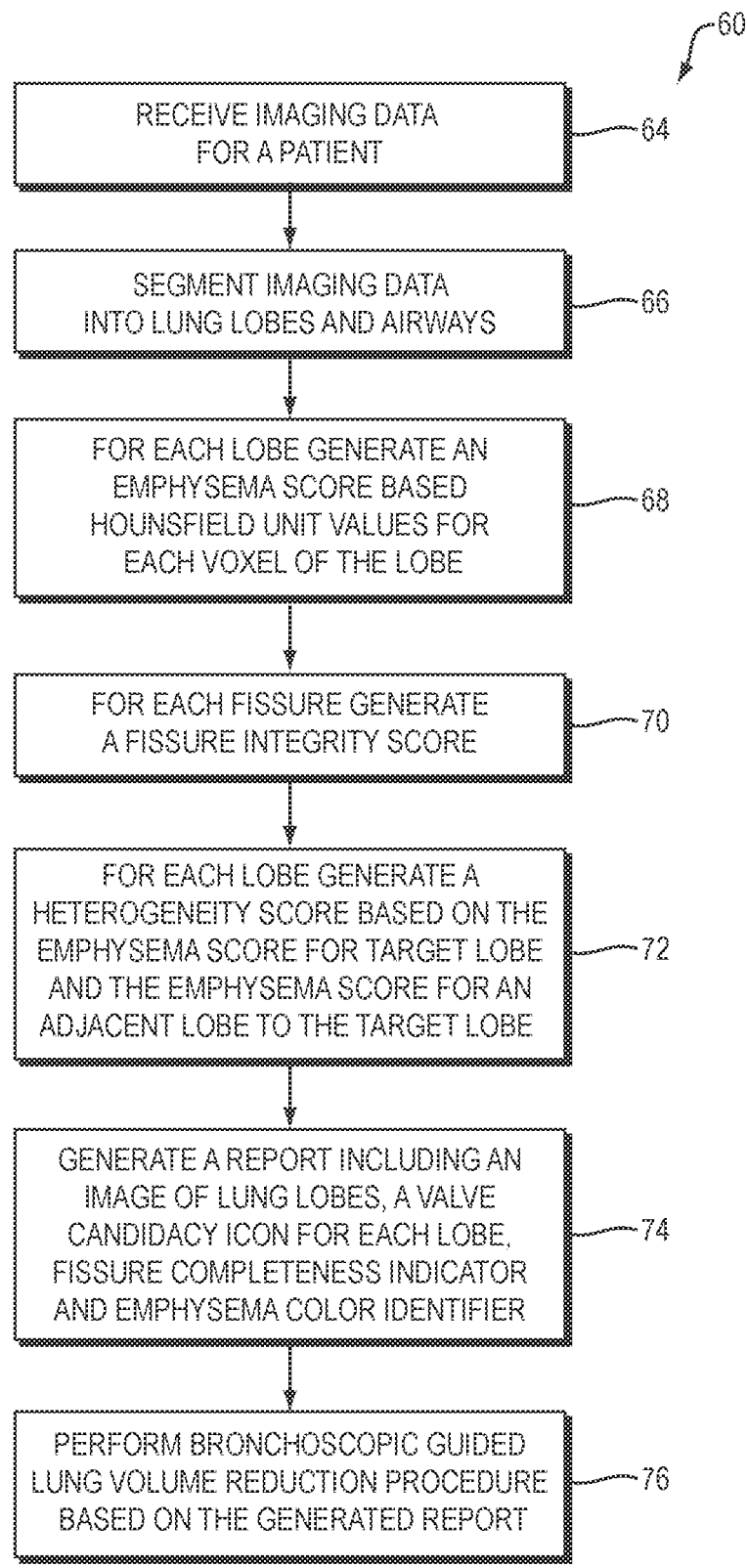
FIG. 2 is a flow diagram of an exemplary process performed by at least the system of FIG. 1.

FIG. 2 shows a flowchart of a lung characterization and visualization method 60 which may be carried out using software as part of the system 10, for example. At a block 64, volumetric radiological images or imaging data of a patient are transmitted to the processing device 40 from the data sources 20. The volumetric radiological images or imaging data may be computed tomography (CT) scans, magnetic resonance imaging (MRI) scans, and/or position emission tomography (PET) scans, from which a series of two-dimensional planar images (referred to herein as two-dimensional volumetric images or two-dimensional images) can be produced in multiple planes. At a block 66, the lungs, airways, and/or blood vessels are segmented using the received image data. The methods of performing lung, airway and vessel segmentation from the volumetric images or imaging data may be those described in various research papers (e.g., Strange C.; Herth, F J; Kovitz, K L; McLennan, G; Ernst, A; Goldin J; et al; Design of the Endobronchial Valve for Emphysema Palliation Trial (VENT): a nonsurgical method of lung volume reduction, BMC Pulm Med. 2007 Jul. 3; 7:10.) Segmentation of the lungs, airways, and vessels results in identification of the lung tissue, airways, and vessels as distinct from the surrounding tissues and of separation of the lungs, airways, and vessels into smaller distinct portions which may be individually identified in accordance with standard pulmonary anatomy. Lung lobes are then delineated from separated data. At a block 68, for each lobe an emphysema score is generated based on Hounsfield unit (i.e., radiodensity (HU)) values for each voxel in the lung lobe data of the targeted lobe. In one embodiment, the emphysema score is identified as a percentage of emphysema in the lobe. The percentage is calculated by determining what percentage of lobe voxels have a Hounsfield unit value less than a threshold amount (e.g. −920 HU) or within a range of Hounsfield unit values. At a block 70, a fissure completeness value is generated for each of three fissures based an analysis of on the imaging data. An exemplary method for calculating the fissure completeness value is described in Brown, M S; Ochs, R; Abtin, F; Ordookhani, A; Brown, M; Kim, H; Shaw, G; Chong, D; Goldin, J. Automated Quantitative Assessment of Lung Fissure Integrity on CT. Proceedings of the First International Workshop on Pulmonary Image Analysis; New York, USA, 2008: 93-102. At a block 72, a heterogeneity score is generated for each lobe based on the difference between the emphysema score for the target lobe and the emphysema score for a lobe adjacent to the target lobe. At a block 74, a report is generated that includes an image that includes BLVR candidacy icons for at least two lobes, fissure completeness indicators and emphysema level visual identifier. At a block 76, a health care provider performs a BLVR procedure, i.e. places one or more interbronchial valves (IBVs) in a lung lobe, based on a review of the generated report. An exemplary IBV is the IBV valve system produced by Olympus®.

Figure 3:
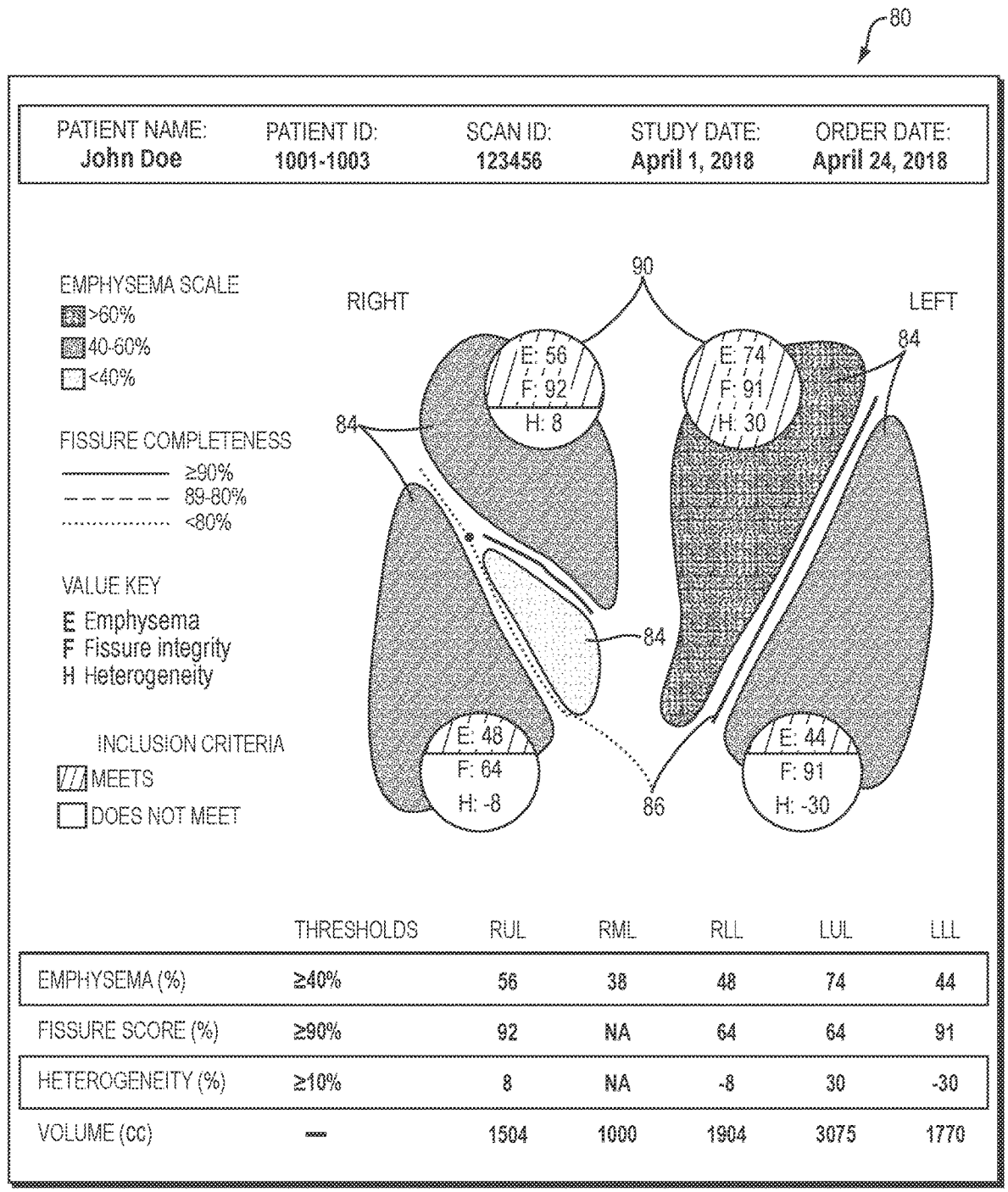
FIG. 3 is an image of a report generated by the system of FIG. 1 in accordance with the process shown in FIG. 2.

FIG. 3 illustrates an exemplary report 80 generated by the processing device 40 (the block 74 of FIG. 2). The report 80 may be generated in any of a number of different formats and delivered any number of different ways to the entity (e.g., health care professional responsible for treating the patient associated with the analyzed image data) who initially made a request for the report. The report 80 includes a lung display area 82 that includes an image of lung lobes 84. The previously calculated emphysema score is represented graphically on the image of the lobes 84 either by a particular pattern or color based on where the emphysema score falls within a predefined scale—see emphysema score scale to the left of the lung display area 82.

Fissure lines 86 are shown between their respective lobes in the lung display area 82. The fissure lines 86 are presented by a particular line pattern and/or color based on the previously calculated fissure completeness score and a fissure completeness scale—see fissure completeness scale shown below the emphysema score scale.

BLVR candidacy icons 90 are shown next to or overlapping the associated lung lobe in the lung display area 82. In this example, the icons 90 are only shown for the right upper lobe, right lower lobe, left upper lobe, and left lower lobe. However, the calculated scores are shown for all lobes in a table at bottom of the report 80. The BLVR candidacy icons 90 include the calculated scores for emphysema, fissure completeness and heterogeneity. The background color or pattern for each score in the icons 90 represent meeting or not meeting a predefined inclusion criteria (i.e., threshold) for each of the scores. The icons 90 provide a visual tool for allowing a health care professional to determine what lobes are good candidates for a BLVR procedure. In the example of FIG. 3, the left upper lobe is the only lobe where all three scores meet the associated predefined criteria (i.e., thresholds). The criteria was determined based on experience gained from multiple clinical trials.

Figure 4:
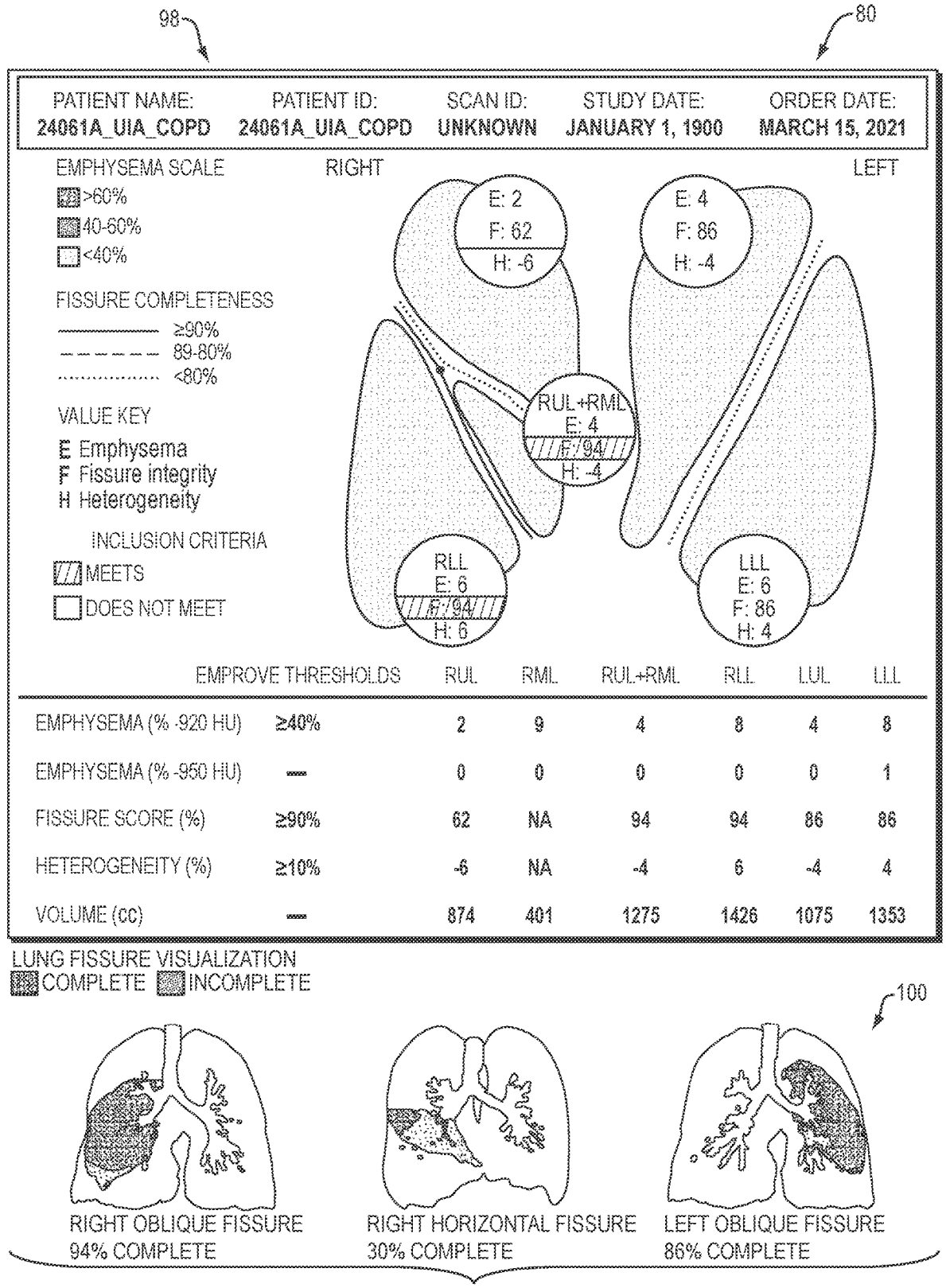
FIG. 4 is an image of a report generated by the system of FIG. 1.

Referring additionally to FIG. 4, a lung report 98 is generated by the processing device 40. The lung report 98 may be generated in any of a number of different formats and delivered any number of different ways to the entity (e.g., health care professional responsible for treating the patient associated with the analyzed image data) who initially made a request for the report. The lung report 98 includes the lung report 80 (FIG. 3) and a lung fissure display area 100.

Figure 5:
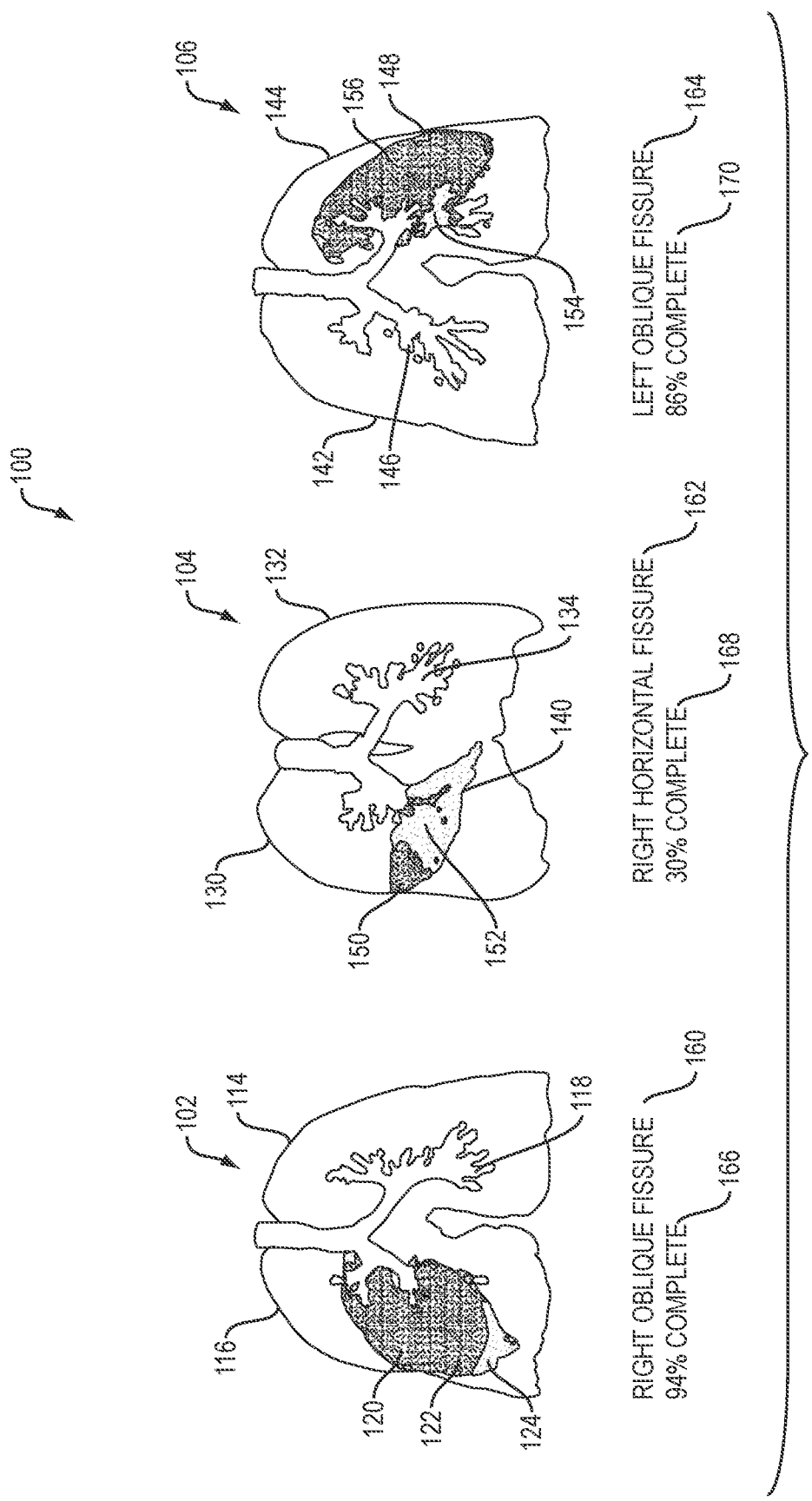
FIG. 5 is an image of a portion of the report of FIG. 4.

Referring additionally to FIG. 5, the lung fissure display area 100 includes three two-dimensional renderings 102, 104, and 106 of lung, airways and fissure information produced by the processing device 40. The first two-dimensional rendering 102 includes a transparent left lung feature 114, a transparent right lung feature 116, a lung airways feature 118, and a right oblique fissure feature 120. The second two-dimensional rendering 104 includes a transparent left lung image feature 132, a transparent right lung feature 130, a lung airways feature 134, and a right horizontal fissure feature 140. The third two-dimensional rendering 106 includes a transparent left lung feature 144, a transparent right lung feature 142, a lung airways feature 146, and a left oblique fissure feature 148.

The processing device 40 categorizes voxels from the volumetric radiological images as lung lobe-type, airway-type, or fissure-type. For each of the two-dimensional renderings 102, 104, and 106 a unique point of view is selected. The processing device 40 generates the two-dimensional renderings 102, 104, and 106 of the categorized voxels based on the unique point of view. It will be appreciated by one of ordinary skill that the two-dimensional renderings of the voxels categorized as lung lobe-type and airway-type need only be determined once and may be reused for each of the two-dimensional renderings 102, 104, and 106 as long as the points of view are equivalent.

The voxels for each of the fissure features (the right oblique fissure feature 120, the right horizontal fissure feature 140, and the left oblique fissure feature 148) are identified as being complete or incomplete. Fissure completeness or incompleteness is based on the previously calculated fissure completeness score and/or a fissure completeness scale. Numbers 122, 150, and 156 point to portions of the fissure features 120, 140, and 148, respectively that are identified as complete. Numbers 124, 152, and 154 point to portions of the fissure features 120, 140, and 148, respectively that are identified as incomplete.

Below the two-dimensional renderings 102, 104, and 106 of the lung fissure display area 100 are fissure labels 160, 162, and 164. The fissure labels 160, 162, and 164 identify the fissure included in the rendering located above the label. The fissure labels 160, 162, and 164 are determined by the processing device 40. Below the fissure labels 160, 162, and 164 are completeness scores 166, 168, and 170 for the respective fissure. The completeness scores 166, 168, and 170 are also determined by the processing device 40 as described above.

Figure 6:
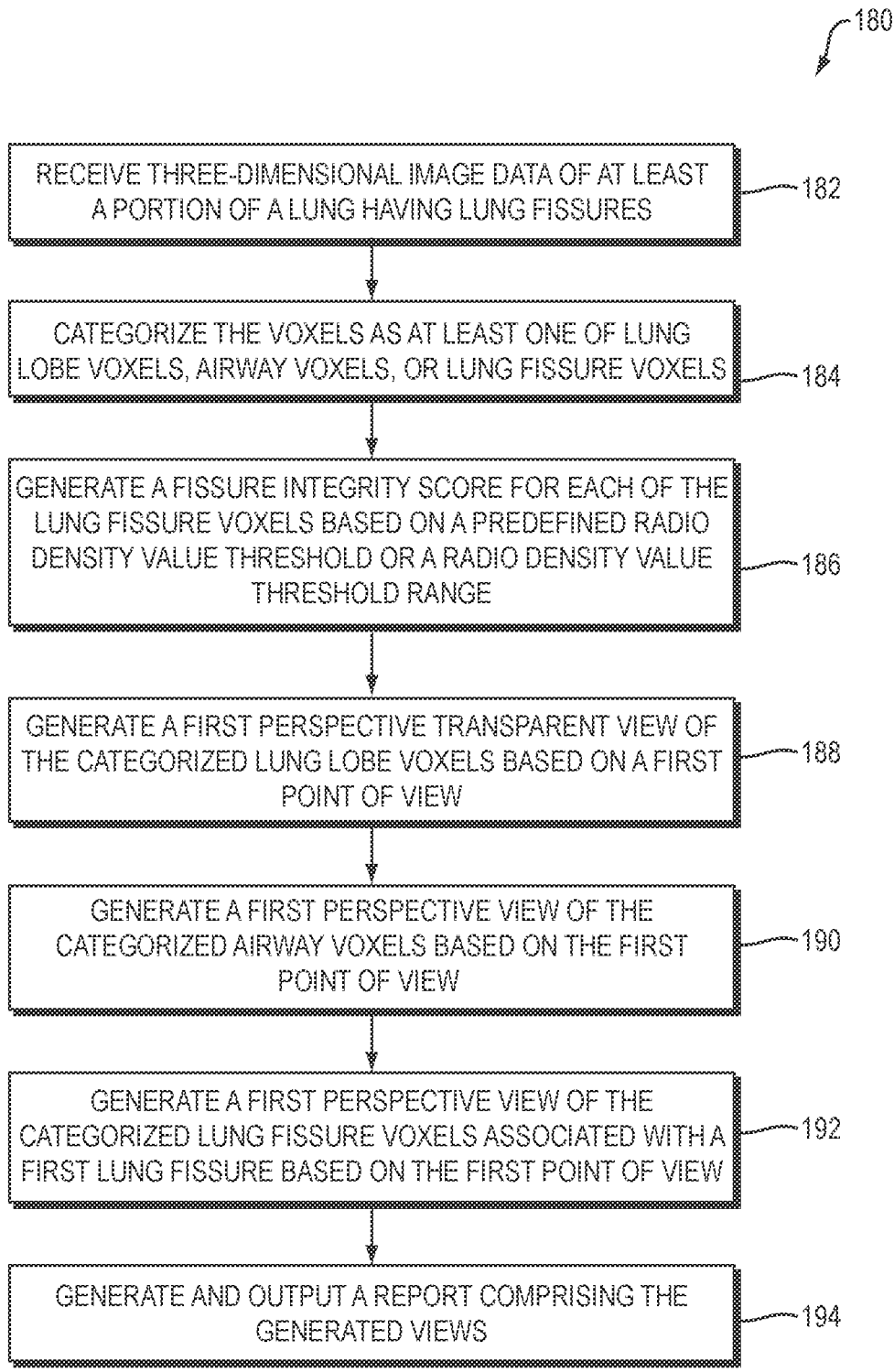
FIG. 6 is a flow diagram of an exemplary process performed by at least the system of FIG. 1.

Referring now to FIG. 6, an illustrative process 180 may be performed for generating two-dimensional images of a lung with fissure integrity information. At a block 182, three-dimensional image data of at least a portion of a lung having lung fissures is received by a processing device. At a block 184, the processing device categorizes the voxels as at least one of lung lobe voxels, airway voxels, or lung fissure voxels. At a block 186, the processing device generates a fissure integrity score for each of the lung fissure voxels based on a predefined radio density value threshold or a radio density value threshold range. At a block 188, the processing device generates a first perspective transparent view of the categorized lung lobe voxels based on a first point of view. At a block 190, the processing device generates a first perspective view of the categorized airway voxels based on the first point of view. At a block 192, the processing device generates a first perspective view of the categorized lung fissure voxels associated with a first lung fissure based on the first point of view. At a block 194, the processing device outputs a report including the generated views.

Blocks 188-194 are repeated for the other fissures included in the three-dimensional image data. Also, the processing device generates fissure labels and a fissure integrity score for each of the fissures represented in the report.

The description of the invention is merely exemplary in nature and variations that do not depart from the gist of the invention are intended to be within the scope of the invention. Such variations are not to be regarded as a departure from the spirit and scope of the invention.

EMBODIMENTS

A. A method comprising: receiving three-dimensional image data of at least a portion of a lung having lung fissures, the three-dimensional image data comprises voxels; categorizing the voxels as at least one of lung lobe voxels, airway voxels, or lung fissure voxels; generating a fissure integrity score for each of the lung fissure voxels based on at least one of a predefined radio density value threshold or a radio density value threshold range; generating a first perspective transparent view of the categorized lung lobe voxels based on a first point of view; generating a first perspective view of the categorized airway voxels based on the first point of view; generating a first fissure perspective view of the categorized lung fissure voxels associated with a first one of the lung fissures based on the first point of view, wherein the first perspective view of the lung fissure voxels includes a visual representation of fissure integrity based on the generated fissure integrity scores for the corresponding voxels; generating a report comprising the generated views; and outputting the report.

B. The method of A, further comprising: determining a fissure completeness score for the first one of the lung fissures based on the generated fissure integrity score for each of the lung fissure voxels corresponding to the first one of the lung fissures; and adding the determined fissure completeness score to the generated report.

C. The method of A, further comprising: generating a second perspective transparent view of the categorized lung lobe voxels based on a second point of view; generating a second perspective view of the categorized airway voxels based on the second point of view; and generating a second perspective view of the categorized lung fissure voxels associated with a second one of the lung fissures based on the second point of view, wherein the second perspective view of the lung fissure voxels includes a visual representation of fissure integrity based on the generated fissure integrity scores for the corresponding voxels.

D. The method of C, further comprising: determining a second fissure completeness score for the second one of the lung fissures based on the generated fissure integrity score for each of the lung fissure voxels corresponding to the second one of the lung fissures; and adding the determined fissure completeness score to the generated report.

E. The method of C, further comprising: generating a third perspective transparent view of the categorized lung lobe voxels based on a third point of view; generating a third perspective view of the categorized airway voxels based on the third point of view; and generating a third perspective view of the categorized lung fissure voxels associated with a third one of the lung fissures based on the third point of view, wherein the third perspective view of the lung fissure voxels includes a visual representation of fissure integrity based on the generated fissure integrity scores for the corresponding voxels.

F. The method of E, further comprising: determining a third fissure completeness score for the third one of the lung fissures based on the generated fissure integrity score for each of the lung fissure voxels corresponding to the third one of the lung fissures; and adding the determined fissure completeness score to the generated report.

G. The method of E, further comprising: generating a fissure label for each of the three lung fissures; and adding the fissure labels to the report.

H. The method of E, wherein generating the report comprises: collocating the first views on the report; collocating the second views on the report; and collocating the third views on the report.

I. A system comprising: a processing device; a memory configured to store computer-readable instructions configured to cause the processing device to: receive three-dimensional image data of at least a portion of a lung having lung fissures, the three-dimensional image data comprises voxels; categorize the voxels as at least one of lung lobe voxels, airway voxels, or lung fissure voxels; generate a fissure integrity score for each of the lung fissure voxels based on at least one of a predefined radio density value threshold or a radio density value threshold range; generate a first perspective transparent view of the categorized lung lobe voxels based on a first point of view; generate a first perspective view of the categorized airway voxels based on the first point of view; generate a first perspective view of the categorized lung fissure voxels associated with a first one of the lung fissures based on the first point of view, wherein the first perspective view of the lung fissure voxels includes a visual representation of fissure integrity based on the generated fissure integrity scores for the corresponding voxels; and generate a report comprising the generated views; and an output device in signal communication with the processing device, the output device configured to output the report.

J. The system of I, wherein the memory is further configured to store computer-executable instructions configured to cause the processing device to: determine a fissure completeness score for the first one of the lung fissures based on the generated fissure integrity score for each of the lung fissure voxels corresponding to the first one of the lung fissures; and add the determined fissure completeness score to the generated report.

K. The system of I, wherein the memory is further configured to store computer-executable instructions configured to cause the processing device to: generate a second perspective transparent view of the categorized lung lobe voxels based on a second point of view; generate a second perspective view of the categorized airway voxels based on the second point of view; and generate a second perspective view of the categorized lung fissure voxels associated with a second one of the lung fissures based on the second point of view, wherein the second perspective view of the lung fissure voxels includes a visual representation of fissure integrity based on the generated fissure integrity scores for the corresponding voxels.

L. The system of K, wherein the memory is further configured to store computer-executable instructions configured to cause the processing device to: determine a second fissure completeness score for the second one of the lung fissures based on the generated fissure integrity score for each of the lung fissure voxels corresponding to the second one of the lung fissures; and add the determined fissure completeness score to the generated report.

M. The system of K, wherein the memory is further configured to store computer-executable instructions configured to cause the processing device to: generate a third perspective transparent view of the categorized lung lobe voxels based on a third point of view; generate a third perspective view of the categorized airway voxels based on the third point of view; and generate a third perspective view of the categorized lung fissure voxels associated with a third one of the lung fissures based on the third point of view, wherein the third perspective view of the lung fissure voxels includes a visual representation of fissure integrity based on the generated fissure integrity scores for the corresponding voxels.

N. The system of M, wherein the memory is further configured to store computer-executable instructions configured to cause the processing device to: determine a third fissure completeness score for the third one of the lung fissures based on the generated fissure integrity score for each of the lung fissure voxels corresponding to the third one of the lung fissures; and add the determined fissure completeness score to the generated report.

O. The system of M, wherein the memory is further configured to store computer-executable instructions configured to cause the processing device to: generate a fissure label for each of the three lung fissures; and add the fissure labels to the report.

P. The system of M, wherein the memory is further configured to store computer-executable instructions configured to cause the processing device to: collocate the first views on the report; collocate the second views on the report; and collocate the third views on the report.

Q. A non-transitory computer-readable recording medium with an executable program stored thereon, the program configured to cause a processor to: receive three-dimensional image data of at least a portion of a lung having lung fissures, the three-dimensional image data comprises voxels; categorize the voxels as at least one of lung lobe voxels, airway voxels, or lung fissure voxels; generate a fissure integrity score for each of the lung fissure voxels based on at least one of a predefined radio density value threshold or a radio density value threshold range; generate a first perspective transparent view of the categorized lung lobe voxels based on a first point of view; generate a first perspective view of the categorized airway voxels based on the first point of view; generate a first perspective view of the categorized lung fissure voxels associated with a first one of the lung fissures based on the first point of view, wherein the first perspective view of the lung fissure voxels includes a visual representation of fissure integrity based on the generated fissure integrity scores for the corresponding voxels; generate a second perspective transparent view of the categorized lung lobe voxels based on a second point of view; generate a second perspective view of the categorized airway voxels based on the second point of view; generate a second perspective view of the categorized lung fissure voxels associated with a second one of the lung fissures based on the second point of view, wherein the second perspective view of the lung fissure voxels includes a visual representation of fissure integrity based on the generated fissure integrity scores for the corresponding voxels; generate a third perspective transparent view of the categorized lung lobe voxels based on a third point of view; generate a third perspective view of the categorized airway voxels based on the third point of view; generate a third perspective view of the categorized lung fissure voxels associated with a third one of the lung fissures based on the third point of view, wherein the third perspective view of the lung fissure voxels includes a visual representation of fissure integrity based on the generated fissure integrity scores for the corresponding voxels; generate a report comprising the generated views; and output the report.

R. The non-transitory computer-readable recording medium of Q, wherein the program being further configured to cause the processor to: determine a fissure completeness score for the first one of the lung fissures based on the generated fissure integrity score for each of the lung fissure voxels corresponding to the first one of the lung fissures; determine a second fissure completeness score for the second one of the lung fissures based on the generated fissure integrity score for each of the lung fissure voxels corresponding to the second one of the lung fissures; determine a third fissure completeness score for the third one of the lung fissures based on the generated fissure integrity score for each of the lung fissure voxels corresponding to the third one of the lung fissures; and add the determined fissure completeness scores to the generated report.

S. The non-transitory computer-readable recording medium of Q, wherein the program being further configured to cause the processor to: generate a fissure label for each of the three lung fissures; and add the fissure labels to the report.

T. The non-transitory computer-readable recording medium of Q, wherein the program being further configured to cause the processor to: collocate the first views on the report; collocate the second views on the report; and collocate the third views on the report.

The term controller/processing device, as used in the foregoing/following disclosure, may refer to a collection of one or more components that are arranged in a particular manner, or a collection of one or more general-purpose components that may be configured to operate in a particular manner at one or more particular points in time, and/or also configured to operate in one or more further manners at one or more further times. For example, the same hardware, or same portions of hardware, may be configured/reconfigured in sequential/parallel time(s) as a first type of controller (e.g., at a first time), as a second type of controller (e.g., at a second time, which may in some instances coincide with, overlap, or follow a first time), and/or as a third type of controller (e.g., at a third time which may, in some instances, coincide with, overlap, or follow a first time and/or a second time), etc. Reconfigurable and/or controllable components (e.g., general purpose processors, digital signal processors, field programmable gate arrays, etc.) are capable of being configured as a first controller that has a first purpose, then a second controller that has a second purpose and then, a third controller that has a third purpose, and so on. The transition of a reconfigurable and/or controllable component may occur in as little as a few nanoseconds, or may occur over a period of minutes, hours, or days.

In some such examples, at the time the processing device is configured to carry out the second purpose, the controller may no longer be capable of carrying out that first purpose until it is reconfigured. A processing device may switch between configurations as different components/modules in as little as a few nanoseconds. A processing device may reconfigure on-the-fly, e.g., the reconfiguration of a processing device from a first processing device into a second processing device may occur just as the second processing device is needed. A processing device may reconfigure in stages, e.g., portions of a first processing device that are no longer needed may reconfigure into the second processing device even before the first processing device has finished its operation. Such reconfigurations may occur automatically, or may occur through prompting by an external source, whether that source is another component, an instruction, a signal, a condition, an external stimulus, or similar.

For example, a central processing unit or the like of a processing device may, at various times, operate as a component/module for displaying graphics on a screen, a component/module for writing data to a storage medium, a component/module for receiving user input, and a component/module for multiplying two large prime numbers, by configuring its logical gates in accordance with its instructions. Such reconfiguration may be invisible to the naked eye, and in some embodiments may include activation, deactivation, and/or re-routing of various portions of the component, e.g., switches, logic gates, inputs, and/or outputs. Thus, in the examples found in the foregoing/following disclosure, if an example includes or recites multiple components/modules, the example includes the possibility that the same hardware may implement more than one of the recited components/modules, either contemporaneously or at discrete times or timings. The implementation of multiple components/modules, whether using more components/modules, fewer components/modules, or the same number of components/modules as the number of components/modules, is merely an implementation choice and does not generally affect the operation of the components/modules themselves. Accordingly, it should be understood that any recitation of multiple discrete components/modules in this disclosure includes implementations of those components/modules as any number of underlying components/modules, including, but not limited to, a single component/module that reconfigures itself over time to carry out the functions of multiple components/modules, and/or multiple components/modules that similarly reconfigure, and/or special purpose reconfigurable components/modules.

In some instances, one or more components may be referred to herein as "configured to," "configured by," "configurable to," "operable/operative to," "adapted/adaptable," "able to," "conformable/conformed to," etc. Those skilled in the art will recognize that such terms (for example "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, " a system having at least one of A, B, and C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software (e.g., a high-level computer program serving as a hardware specification), firmware, or virtually any to patentable subject matter under 35 U.S.C. 101. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. 101, and that designing the circuitry and/or writing the code for the software (e.g., a high-level computer program serving as a hardware specification) and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

With respect to the appended claims, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While the disclosed subject matter has been described in terms of illustrative embodiments, it will be understood by those skilled in the art that various modifications can be made thereto without departing from the scope of the claimed subject matter as set forth in the claims.

What is claimed is:

1. A method for computer generation of a lung report, the method comprising:
   receiving, into memory on a computer, three-dimensional image data of at least a portion of a lung having lung fissures, the three-dimensional image data comprises voxels;
   categorizing, on a processor accessing the memory on the computer, the voxels as at least one of lung lobe voxels, airway voxels, or lung fissure voxels;
   generating, on the processor accessing the memory on the computer, a fissure integrity score for each of the lung fissure voxels based on at least one of a predefined radio density value threshold or a radio density value threshold range;
   generating, on the processor accessing the memory on the computer, a first perspective transparent view of the categorized lung lobe voxels based on a first point of view;
   generating, on the processor accessing the memory on the computer, a first perspective view of the categorized airway voxels based on the first point of view;
   generating, on the processor accessing the memory on the computer, a first fissure perspective view of the categorized lung fissure voxels associated with a first one of the lung fissures based on the first point of view, wherein the first perspective view of the lung fissure voxels includes a visual representation of fissure integrity based on the generated fissure integrity scores for the corresponding voxels;
   generating, on the processor accessing the memory on the computer, a lung report including a lung display area and a lung fissure display area, the lung fissure display area comprising the first perspective transparent view of the categorized lung lobe voxels, the first perspective view of the categorized airway voxels, and the first fissure perspective view of the categorized lung fissure voxels; and
   outputting the report.

2. The method of claim 1, further comprising:
   determining a fissure completeness score for the first one of the lung fissures based on the generated fissure integrity score for each of the lung fissure voxels corresponding to the first one of the lung fissures; and
   adding the determined fissure completeness score to the generated report.

3. The method of claim 1, further comprising:
   generating a second perspective transparent view of the categorized lung lobe voxels based on a second point of view;
   generating a second perspective view of the categorized airway voxels based on the second point of view; and
   generating a second perspective view of the categorized lung fissure voxels associated with a second one of the lung fissures based on the second point of view, wherein the second perspective view of the lung fissure voxels includes a visual representation of fissure integrity based on the generated fissure integrity scores for the corresponding voxels.

4. The method of claim 3, further comprising:
   determining a second fissure completeness score for the second one of the lung fissures based on the generated fissure integrity score for each of the lung fissure voxels corresponding to the second one of the lung fissures; and
   adding the determined fissure completeness score to the generated report.

5. The method of claim 3, further comprising:
   generating a third perspective transparent view of the categorized lung lobe voxels based on a third point of view;
   generating a third perspective view of the categorized airway voxels based on the third point of view; and
   generating a third perspective view of the categorized lung fissure voxels associated with a third one of the lung fissures based on the third point of view, wherein the third perspective view of the lung fissure voxels includes a visual representation of fissure integrity based on the generated fissure integrity scores for the corresponding voxels.

6. The method of claim 5, further comprising:
   determining a third fissure completeness score for the third one of the lung fissures based on the generated fissure integrity score for each of the lung fissure voxels corresponding to the third one of the lung fissures; and
   adding the determined fissure completeness score to the generated report.

7. The method of claim 5, further comprising:
   generating a fissure label for each of the three lung fissures; and
   adding the fissure labels to the report.

8. The method of claim 5, wherein generating the report comprises:
   collocating the first views on the report;
   collocating the second views on the report; and
   collocating the third views on the report.

9. A system comprising:
   a processing device;
   a memory configured to store computer-readable instructions configured to cause the processing device to:
   receive three-dimensional image data of at least a portion of a lung having lung fissures, the three-dimensional image data comprises voxels;
   categorize the voxels as at least one of lung lobe voxels, airway voxels, or lung fissure voxels;
   generate a fissure integrity score for each of the lung fissure voxels based on at least one of a predefined radio density value threshold or a radio density value threshold range;
   generate a first perspective transparent view of the categorized lung lobe voxels based on a first point of view;
   generate a first perspective view of the categorized airway voxels based on the first point of view;
   generate a first perspective view of the categorized lung fissure voxels associated with a first one of the lung fissures based on the first point of view, wherein the first perspective view of the lung fissure voxels includes a visual representation of fissure integrity based on the generated fissure integrity scores for the corresponding voxels; and generate a lung report including a lung display area and a lung fissure display area, the lung fissure display area comprising the first perspective transparent view of the categorized lung lobe voxels, the first perspective view of the categorized airway voxels, and the first fissure perspective view of the categorized lung fissure voxels; and an output device in signal communication with the processing device, the output device configured to output the report.

10. The system of claim 9, wherein the memory is further configured to store computer-executable instructions configured to cause the processing device to:

determine a fissure completeness score for the first one of the lung fissures based on the generated fissure integrity score for each of the lung fissure voxels corresponding to the first one of the lung fissures; and add the determined fissure completeness score to the generated report.

11. The system of claim 9, wherein the memory is further configured to store computer-executable instructions configured to cause the processing device to:

generate a second perspective transparent view of the categorized lung lobe voxels based on a second point of view;

generate a second perspective view of the categorized airway voxels based on the second point of view; and generate a second perspective view of the categorized lung fissure voxels associated with a second one of the lung fissures based on the second point of view, wherein the second perspective view of the lung fissure voxels includes a visual representation of fissure integrity based on the generated fissure integrity scores for the corresponding voxels.

12. The system of claim 11, wherein the memory is further configured to store computer-executable instructions configured to cause the processing device to:

determine a second fissure completeness score for the second one of the lung fissures based on the generated fissure integrity score for each of the lung fissure voxels corresponding to the second one of the lung fissures; and add the determined fissure completeness score to the generated report.

13. The system of claim 11, wherein the memory is further configured to store computer-executable instructions configured to cause the processing device to:

generate a third perspective transparent view of the categorized lung lobe voxels based on a third point of view;

generate a third perspective view of the categorized airway voxels based on the third point of view; and generate a third perspective view of the categorized lung fissure voxels associated with a third one of the lung fissures based on the third point of view, wherein the third perspective view of the lung fissure voxels includes a visual representation of fissure integrity based on the generated fissure integrity scores for the corresponding voxels.

14. The system of claim 13, wherein the memory is further configured to store computer-executable instructions configured to cause the processing device to:

determine a third fissure completeness score for the third one of the lung fissures based on the generated fissure integrity score for each of the lung fissure voxels corresponding to the third one of the lung fissures; and add the determined fissure completeness score to the generated report.

15. The system of claim 13, wherein the memory is further configured to store computer-executable instructions configured to cause the processing device to:

generate a fissure label for each of the three lung fissures; and add the fissure labels to the report.

16. The system of claim 13, wherein the memory is further configured to store computer-executable instructions configured to cause the processing device to:

collocate the first views on the report;

collocate the second views on the report; and collocate the third views on the report.

17. A non-transitory computer-readable recording medium with an executable program stored thereon, the program configured to cause a processor to:

receive three-dimensional image data of at least a portion of a lung having lung fissures, the three-dimensional image data comprises voxels;

categorize the voxels as at least one of lung lobe voxels, airway voxels, or lung fissure voxels;

generate a fissure integrity score for each of the lung fissure voxels based on at least one of a predefined radio density value threshold or a radio density value threshold range;

generate a first perspective transparent view of the categorized lung lobe voxels based on a first point of view;

generate a first perspective view of the categorized airway voxels based on the first point of view;

generate a first perspective view of the categorized lung fissure voxels associated with a first one of the lung fissures based on the first point of view, wherein the first perspective view of the lung fissure voxels includes a visual representation of fissure integrity based on the generated fissure integrity scores for the corresponding voxels;

generate a second perspective transparent view of the categorized lung lobe voxels based on a second point of view;

generate a second perspective view of the categorized airway voxels based on the second point of view;

generate a second perspective view of the categorized lung fissure voxels associated with a second one of the lung fissures based on the second point of view, wherein the second perspective view of the lung fissure voxels includes a visual representation of fissure integrity based on the generated fissure integrity scores for the corresponding voxels;

generate a third perspective transparent view of the categorized lung lobe voxels based on a third point of view;

generate a third perspective view of the categorized airway voxels based on the third point of view;

generate a third perspective view of the categorized lung fissure voxels associated with a third one of the lung fissures based on the third point of view, wherein the third perspective view of the lung fissure voxels includes a visual representation of fissure integrity based on the generated fissure integrity scores for the corresponding voxels;

generate a lung report including a lung display area and a lung fissure display area, the lung fissure display area comprising the first through third perspective transparent views of the categorized lung lobe voxels, the first through third perspective views of the categorized airway voxels, and the first through third fissure perspective views of the categorized lung fissure voxels collocated within the lung report; and output the report.

18. The non-transitory computer-readable recording medium of claim 17, wherein the program being further configured to cause the processor to:

determine a fissure completeness score for the first one of the lung fissures based on the generated fissure integrity score for each of the lung fissure voxels corresponding to the first one of the lung fissures;

determine a second fissure completeness score for the second one of the lung fissures based on the generated fissure integrity score for each of the lung fissure voxels corresponding to the second one of the lung fissures;

determine a third fissure completeness score for the third one of the lung fissures based on the generated fissure integrity score for each of the lung fissure voxels corresponding to the third one of the lung fissures; and add the determined fissure completeness scores to the generated report.

19. The non-transitory computer-readable recording medium of claim 17, wherein the program being further configured to cause the processor to:

generate a fissure label for each of the three lung fissures; and add the fissure labels to the report.

* * * * *